(12) United States Patent
Saberton et al.

(10) Patent No.: US 12,053,555 B2
(45) Date of Patent: *Aug. 6, 2024

(54) AIRCRAFT DISINFECTING DEVICE

(71) Applicant: Addman Engineering, Bonita Springs, FL (US)

(72) Inventors: Mark Saberton, Bonita Springs, FL (US); Matthew Saberton, Bonita Springs, FL (US); Stephen Glaudel, Hatfield, PA (US)

(73) Assignee: Addman Intermediate Holdings, LLC, Fort Myers, FL (US)

( * ) Notice: Subject to any disclaimer, the term of this patent is extended or adjusted under 35 U.S.C. 154(b) by 419 days.

This patent is subject to a terminal disclaimer.

(21) Appl. No.: 17/518,910

(22) Filed: Nov. 4, 2021

(65) Prior Publication Data

US 2022/0193279 A1    Jun. 23, 2022

Related U.S. Application Data

(60) Provisional application No. 63/127,590, filed on Dec. 18, 2020.

(51) Int. Cl.
| *A61L 2/10* | (2006.01) |
| *A61L 2/24* | (2006.01) |
| *A61L 2/26* | (2006.01) |
| *B64D 47/02* | (2006.01) |
| *B64F 5/30* | (2017.01) |
| *G01P 13/00* | (2006.01) |

(52) U.S. Cl.
CPC ...... *A61L 2/10* (2013.01); *A61L 2/24* (2013.01); *A61L 2/26* (2013.01); *B64D 47/02* (2013.01); *B64F 5/30* (2017.01); *G01P 13/00* (2013.01); *A61L 2202/11* (2013.01); *A61L 2202/14* (2013.01); *A61L 2202/16* (2013.01); *A61L 2202/25* (2013.01)

(58) Field of Classification Search
CPC ...... A61L 2/10; A61L 2/24; A61L 2/26; A61L 2202/11; A61L 2202/14; A61L 2202/16; A61L 2202/25; B64F 5/30; B64D 47/02; G01P 13/00
USPC ................. 250/453.11, 454.11, 455.11
See application file for complete search history.

(56) References Cited

U.S. PATENT DOCUMENTS

2023/0241268 A1* 8/2023 Saberton .............. A61L 2/10

* cited by examiner

*Primary Examiner* — Nicole M Ippolito (57) ABSTRACT

The present invention provides a fixture or device which is particularly adapted for installation within a general aviation aircraft, such as a small private jet, prop-driven plane, helicopter, spacecraft, or other aviation vehicle, and which emits UV-C within safe limits, i.e., within prescribed safe wavelengths, irradiance, and times (below the 'Actinic Dose') while the aircraft is occupied, to continuously disinfect the interior air and prevent transmission by not only the COVID-19 virus but other viruses as well. The device, generally, comprises a two-piece or two-part assembly, having a base and a cover which mounts to the ceiling or wall(s) of an aircraft. A UV-C lamp, typically an LED, is disposed within the fixture and projects it therefrom into the cabin, as well as control-electronics to ensure safe emission limits by the LED.

9 Claims, 7 Drawing Sheets

AIRCRAFT DISINFECTING DEVICE

CROSS-REFERENCE TO RELATED APPLICATION

This application is a completion application which claims the priority benefit of U.S. Provisional Patent Application Ser. No. 63/127,590, filed Dec. 18, 2020, for "Aircraft Disinfecting Device", the disclosure of which is hereby incorporated by reference in its entirety, including the drawing.

BACKGROUND OF THE INVENTION

1. Field of the Invention

The present invention concerns disinfecting devices for use in the interiors of spacecraft, aircraft, helicopters and the like. More particularly, the present invention concerns disinfecting devices particularly for such interiors using UV light. Even more particularly, the present invention concerns UV light emitting devices for destroying viruses within the tight confines of the highly regulated industries of spacecraft, aircraft, helicopters and the like.

2. Prior Art

As the world finds itself within the throes of a pandemic attributable to the COVID-19 virus, much attention has been directed to developing therapeutics and vaccines to thwart the effects of the virus. In parallel, much attention has been directed to thwart the transmission of the virus. Typically, this has been done via 'sterilization' of surfaces, coupled with the wearing of masks and face-shields to prevent droplets and aerosols from a contagious person, even if asymptomatic, from impacting and infecting another person. 'Distancing' is also an effective means of limiting transmission via aerosols. However, the tight confines of aircraft make this attempt impossible.

The aviation industry is one of the more devastated industries attributable to the effects and/or fears of this virus. It has now become commonplace to disinfect touch-surfaces in between flights. Yet, that is not the primary mode of infection for COVID-19.

It is extraordinarily difficult to disinfect the interior of an aircraft after passengers come aboard, and exchange aerosols with other passengers, due to the air which is continuously being circulated within the interior of the aircraft. Yet, it is essential that such aircraft, including spacecraft, helicopters, as well as airplanes and, especially general aviation aircraft, be capable of flying under 'safe' conditions, not only mechanically but also hygienically.

It is now generally accepted that the COVID-19 virus, as well as many other viruses are spread as aerosols, i.e., directly from human-to-human. More specifically, the multiple families of RNA-based viruses which mutate rapidly and, thus, are less well alleviated by vaccines are responsible for most of the modern world's epidemics and pandemics, as well as less-dangerous but still economically deleterious 'sick-time', e.g., Corona, Influenza, Pneumovirus, Rhinovirus, ad nauseum. As a consequence, the disinfecting of surfaces as an intermediary between human touches does not prevent the spread of these viruses between persons, especially within the tight confines of an aircraft. So, even if the seats, tabletops, walls and ceilings and other surfaces have been, or are continuously being disinfected, this does not preclude the spread of these viruses.

Ultraviolet light comes in a range of wavelengths (100-400 nm). Likewise, pathogens come in many forms. While it is known that some UV-A wavelengths (from 315-400 nm) can destroy some bacteria and fungi, e.g. HAIs: Healthcare Associated Infections such as MRSA, it is not effective against most non-metabolizing pathogens, e,g., viruses, which are noted above. UV-A does not target the reduced biochemical-complement of these much-smaller pathogens since they cannot exist very long outside of a host.

Also, it is well known that ultraviolet light in UV-C wavelengths (from 200-280 nm) can destroy not only corona viruses, including COVID-19, but all known viruses. Also, at somewhat higher 'doses', i.e., irradiance-levels over time, measured in Joules per square-meter, UV-C can also kill larger alive, metabolizing pathogens such as bacteria/fungi and protists. UV-C does this by direct impingement on nucleic-acids (RNA/DNA) causing them to become incapable of being copied for either replication/transcription, or protein-translation. More specifically, there is copious published documentation of nucleic-acid absorption (i.e., relating to Pathogen 'kill rates') using UV-C wavelengths around 254 nm. Thus, there has been widespread use over many decades of UV-C light emitting devices such as, for example, high-powered mercury arc-lamps which are used to sterilize drinking water. However, known prior art devices, generally, do not control the time/dosage/proximity of a person to such a UV-C source.

Ultraviolet 'Controls' are extremely important since UV-C has a hazardous effect upon both the skin and eyes of persons who are exposed to high doses' (high irradiance, or extended times) of it. Typically, humans cannot be in the vicinity of high-powered sterilization devices, such as mercury arc-lamps even for a time frame of seconds.

A globally-recognized photobiological safety specification IEC-62471 has been available for many years to document the limits of UV-C human exposures. This 'Actinic Dose' is defined as the continual maximum of 30 Joules per square-meter, over the course of 24 hours.

Published data demonstrates the rates at which many different pathogens can be disabled, even with UV-C below the 'Actinic Dose', i.e., disinfecting lighting, even when a space is human-occupied. Thus, it is to be readily appreciated that if the requisite dose controls (irradiance×exposure time) for continuously disinfecting the air within an environment with UV-C light, where people congregate, such as in aircraft and spacecraft, then a major tool would be provided in the battle against multiple pathogens, including COVID-19, especially for use within tightly confined spaces.

It is to this to which the present invention is directed.

SUMMARY OF THE INVENTION

The present invention provides a fixture or device which is particularly adapted for installation within a general aviation aircraft, such as a small private jet, prop-driven plane, helicopter, spacecraft, or other aviation vehicle, and which emits UV-C within safe limits, i.e., within prescribed safe wavelengths, irradiance, and times (below the 'Actinic Dose') while the aircraft is occupied, to continuously disinfect the interior air and prevent transmission by not only the COVID-19 virus but other viruses as well.

The device, generally, comprises a two-piece or two-part assembly, having a base and a cover which mounts to the ceiling or wall(s) of an aircraft. A UV-C lamp, typically an LED, is disposed within the fixture and projects it therefrom into the cabin, as well as control-electronics to ensure safe emission limits by the LED.

A ring or collar sandwiches the ceiling or wall around the device between the base and the collar to the device thereto.

The device is FAA compliant and thus is not debilitated by vibration or compression.

For a more complete understanding of the present invention reference is made to the following description of the invention and accompanying drawing.

In the drawing like reference characters refer to like parts throughout the several views in which:

BRIEF DESCRIPTION OF THE DRAWINGS

FIG. 7B is a second perspective view of the device hereof with the cover removed in;

DESCRIPTION OF THE INVENTION

At the outset it is to be noted that the ensuing description will be made with reference to an "aircraft". However, it is to be understood that as used herein the term "aircraft" includes, both general and commercial airplanes, helicopters, spacecraft and the like.

Now, and with reference to the drawings in FIGS. 1-6, depicted therein is an embodiment of the present disinfecting device or fixture and which is generally denoted at 10.

Figure 1:
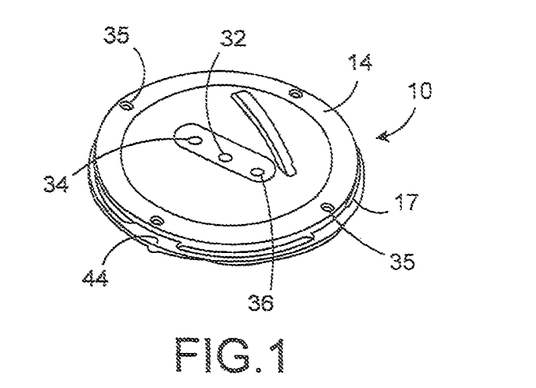
FIG. 1 is a partial exploded view of a first embodiment of a disinfecting device in accordance with the present invention.
Figure 2:
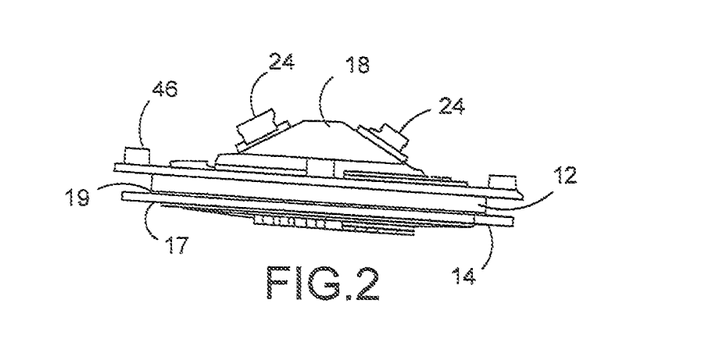
FIG. 2 is a side view thereof.
Figure 3:
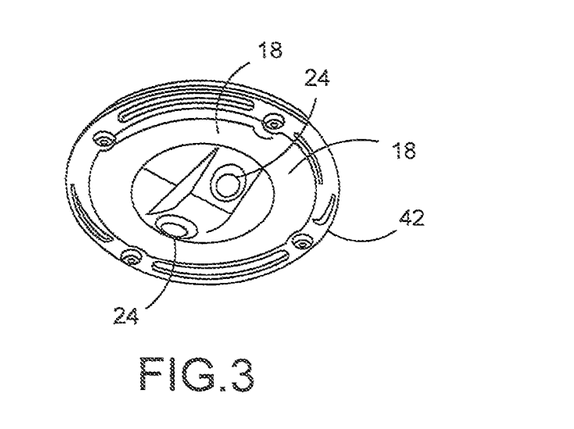
FIG. 3 is a perspective view of the bottom of the disinfector.
Figure 4:
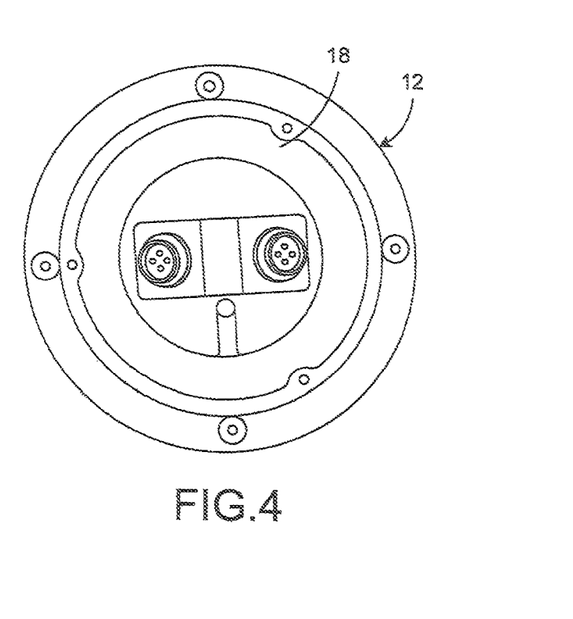
FIG. 4 is a plan view of the bottom thereof.

As shown, the device 10 generally comprises a base 12 and a cover or cover plate 14. The base has an upper surface 16 and a lower surface 18. The cover 14 has an outer surface 17 and an interior or lower surface 19.

Figure 6:
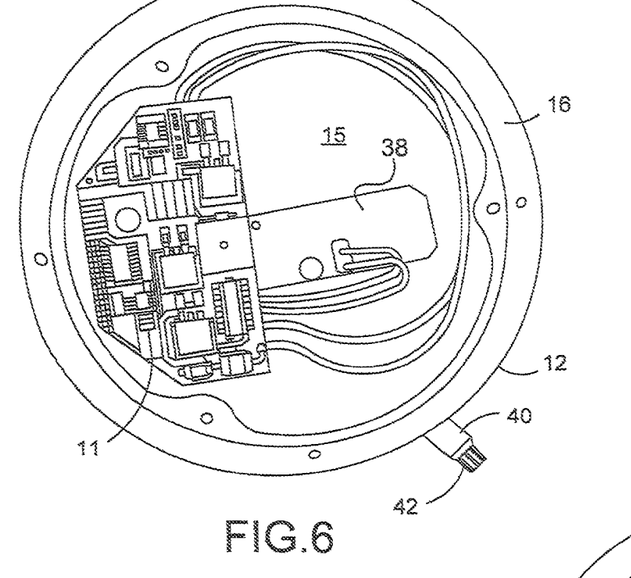
FIG. 6 is a plan view of the interior chamber of the device.

As shown in FIG. 6, an interior space or chamber 15 is provided between the upper or interior surface 16 of the base 12 and the interior surface 19 of the cover 14. A mounting plate is secured to the interior surface and is used to mount and secure the various components of the fixture to the device.

The base 12 is a substantially circular member which is used to affix the device to the interior roof or ceiling of the fuselage of an aircraft. It should be noted that although the present device is depicted as circular, it can take on other geometric configurations, including rectangular, ovoid, hexagonal, etc.

Ordinarily, and as discussed below a Printed Circuit Board or pcBoard 11 is disposed in the chamber 15 and to which plugs, or other connectors are connected for powering the components and communicating signals from device to device.

As is known to those skilled in the art to which the present invention pertains typically electrical harnesses for stringing wiring, powering pumps, cooling fans, etc. are disposed in the space between the interior compartment ceiling/walls and the fuselage skin and, thus, defines a utilities space (not shown) and which traverses the roof of the fuselage within the passenger compartment.

The lower surface of the base 12 seats against the interior roof or ceiling and is used to connect the present device to the electrical system of the aircraft within the passenger compartment and cockpit, as discussed hereinbelow.

As shown, a pair of spaced apart plugs 24 are mounted to the outer surface of the base 12 and are disposed within the utilities space. Due to FAA regulations the plug(s) are, preferably, Cannon plugs which are well-known and commercially available or may be other FAA certified connectors needed which are to be used to electrically interconnect the electrical components of the present device to a conventional electrical harness (not shown) disposed in the utilities space.

Lead wires extend from the plug(s) 24 to the components of the device and the pcBoard 11 housed within the chamber 15.

Figure 5:
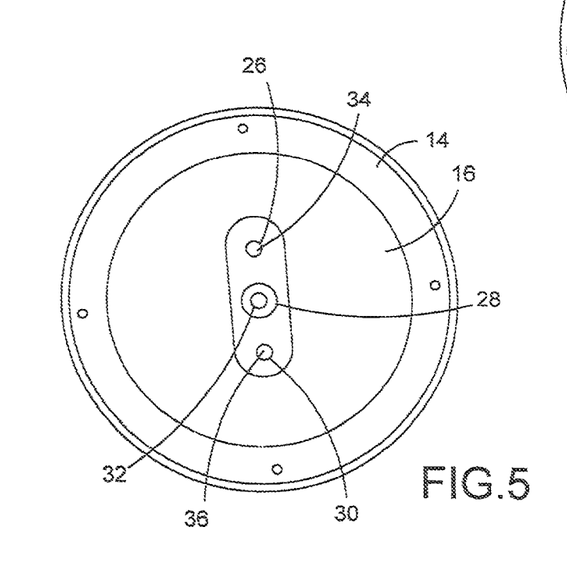
FIG. 5 is a plan view of the cover thereof.

Openings, such as opening 26, are formed in the cover 14 (FIG. 5).

Referring to FIG. 1 at least one UV-C LED lamp 32 is housed within the chamber 15. The UV-C LED lamp is connected to the printed circuit board 11 and projects through an associated opening 28 in the cover and is used to emit UV-C light into the passenger compartment of the aircraft.

Optimally, at least one and, preferably, two or more other visual wavelength distinct colored LED lamps 36 are similarly connected and project their beams through associated openings 30, 34 in the cover 14 and are used as indicators to identify the status of the UV-C lamp 32. For example, LED colors, such as green, yellow and red may be used to indicate the "On-off", "Disinfecting", and "Unsafe irradiance" statuses, respectively. Alternatively, a single status indicator light coupled to a status switch may be used as described below.

Also, means for emitting an audible signal may be provided and be used to emit a sound in case of "Unsafe irradiance" along with a designated LED may be used, so that either a blind or a deaf passenger can know to exit the aircraft (if practical), and/or the crew can know to disconnect electrical power via a kill-switch connected to the fixture.

Irradiance is related to the physical distance between the UV emitter and a 'target', such as, a floor, but the target can also be a passenger, a food-tray, or the like, according to the Inverse-Square-Law of Physics.

In practicing the present invention, the UV-C irradiance level is chosen so that passengers in their 'normal' positions, i.e., seated, away from the aisle, will always receive less than the 'Actinic Dose'. However, given the low ceiling height of an aircraft compared to the height of a typical passenger, of about 6 feet, a passenger walking/standing/lingering directly beneath the device or fixture 10 is in an unsafe position. Thus, and referring, again, to FIG. 1, the present invention includes means for redirecting irradiance by dimming or turning off the UV-C emitter via a controller 38 (FIG. 6).

A motion sensor or detector 40 is connected to the pcBoard 11 and is mounted to the cover 14 and is used to sense the presence of an object, such as, a person, animal or the like in potentially dangerous proximity to the UV-C light emitted by UV-C lamp 32.

The motion sensor 40 is, preferably, a Passive Infrared (PIR) motion sensor, which senses the presence of a living object, i.e., a person or animal as being too close to the UV-C lamp 32 and signals the lamp 32 to be either dimmed or shut-off, unless and until the sensor indicates absence of that person.

Figure 11:
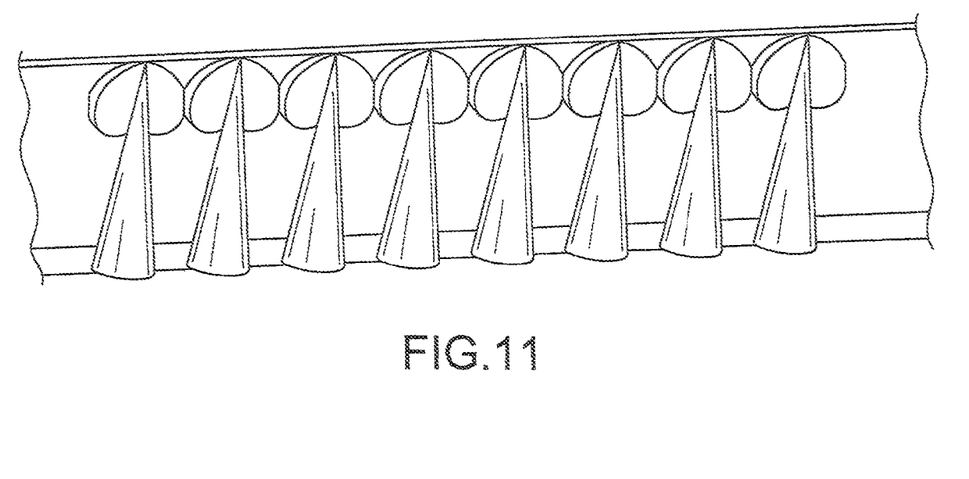
FIG. 11 is a geographical display showing the irradiance when an aircraft cabin is unoccupied.

As shown in FIG. 11, the emitting range or pattern of the LED lamps 32 is typically conical. Thus, in order to control the shape of the PIR sensing range, an aspherical lens or shroud 42 envelops the sensor to control or direct the area to be covered. Alternatively, and as discussed hereinbelow an opening or aperture may be formed in the cover and be used to control the sensing range when the light is emitted therethrough.

Preferably, this PIR sensor 40 detects the presence of an object in the aisle of the aircraft or its nearness to the ceiling and communicates that to the electronic controller 38 for the UV-C lamp 32 to either dim it or shut it off. Since a passenger plane almost always uses a 'cylindrical' fuselage (i.e., its ceiling lowers as one is farther from the aisle), geometry dictates that a passenger seated away from the aisle will be incapable of standing, and so will receive a safe and effective UV-C disinfecting dose (i.e., below the 'Actinic limit'). It is possible to use two or more PIR motion sensors within each fixture for redundancy or for shaping the sensing range.

Optionally, selective cable connections may be used to enable the presence or motion sensor to be employed not only to dim/shut-off the UV-C lamp with this same device, but to also have the same effect on adjacent devices (i.e., down-aisle and up-aisle). Thus, when a passenger or crew-member is detected proximate the ceiling or in the aisle the forward device and the rearward fixture near the object, in addition to the detecting sensor, are automatically shut off. Once the passenger is outside the detection area, the LEDs are turned back on. This option can provide a degree of redundancy of presence detection if fixtures are mounted with overlapping sensor presence-detection cones/ovoids. Such option can also provide for earlier detection of passengers walking down the aisle, thereby lowering the UV-C irradiance just ahead of where he/she is about to go.

In practicing the present invention, preferably, at least two sensors [[40' 40']] with overlapping sensing regions, one 'aiming' up-aisle and one 'aiming' more down-aisle may be deployed. This enables the same safety redundancy, but with no requirement for device to device mounting adjacency.

It is also possible to deploy a pair of spaced apart UV-C LEDs arrayed in series. Here, the LED's which are in electrical communication with the PIR sensors, are angularly disposed at a tilt angle of about 30° to 60° to provide a greater device to device spacing and longer UV-C raylengths. This results in greater disinfecting air volume.

It should be noted that the tilt angle of the UV-C emitters must match the PIR sensing angle for objects approaching down the aisle.

Once the presence of a human/object is no longer sensed, the UV-C lamp 32 becomes operative again.

It is to be appreciated that the UV-C lamp 32 continues to emit its beam proximate the seated object and is only disrupted by a person or animal within the volume of the sensing range.

As noted, the presence detector is preferably a passive infrared sensor (PIR). However, a Time-of-Flight or similar sensor can be deployed with equal efficacy as the LiDar sensors.

Referring again to FIGS. 1 and 2, as shown, the cover 14 mates with the base 12 and is detachably connected and secured thereto by any suitable means, such as threaded fasteners or the like through openings 35.

Similarly, the base 12 is fixed to the interior roof or ceiling of the fuselage through threaded fasteners or the like. Here, a collar 19 is emplaced in the utility space and has openings 44 which align with registering apertures 46 provided in the base. Threaded fasteners then secure the base to the collar thereby sandwiching that portion of the ceiling therebetween.

Referring now to FIGS. 7A through 12 there is depicted therein a second embodiment of the present invention, generally, denoted at 110. In accordance herewith the device includes a housing 112 having an upper outwardly facing top surface 114, a cylindrical sidewall 115 and a rear surface or cover 116. FIG. 7B shows the device having an open interior 143 in which a mounting assembly 141 (FIGS. 8 and 10) having the necessary components is mounted thereto, as discussed below.

Figure 7A:
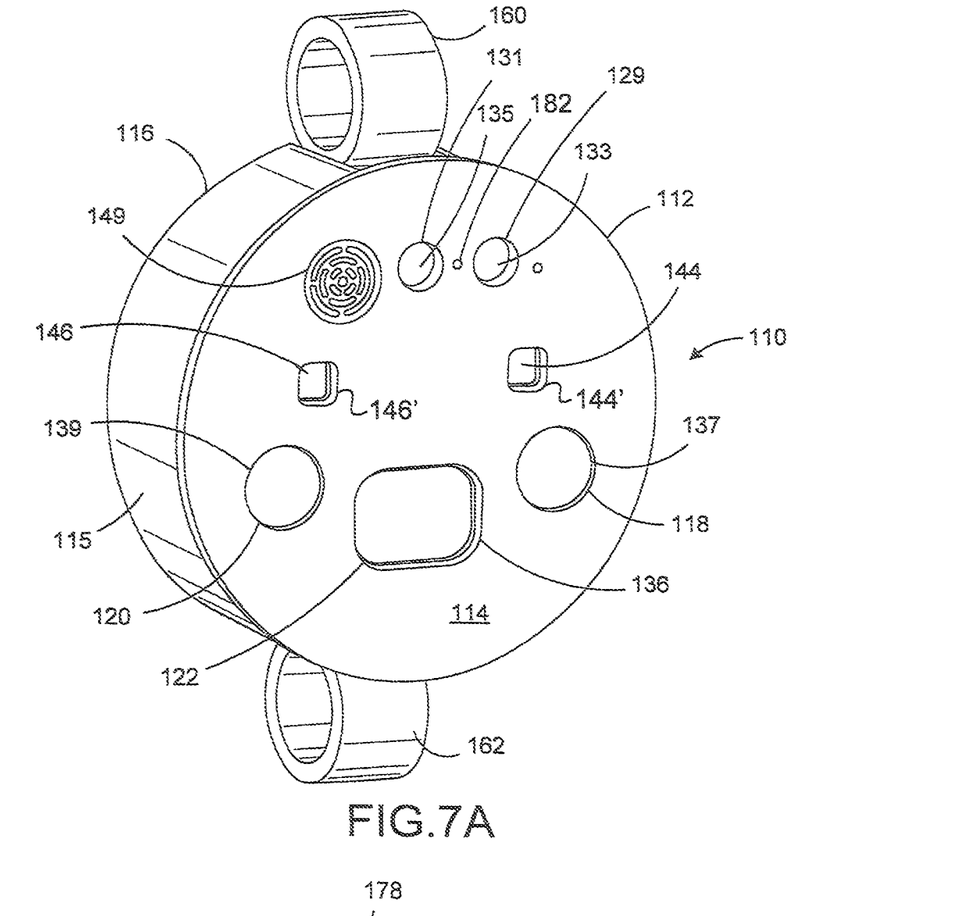
FIG. 7A is a first perspective view of a housing used in a second embodiment hereof.
Figure 7B:
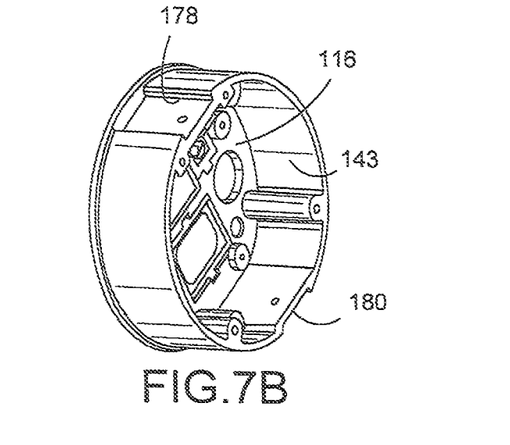
Figure 10:
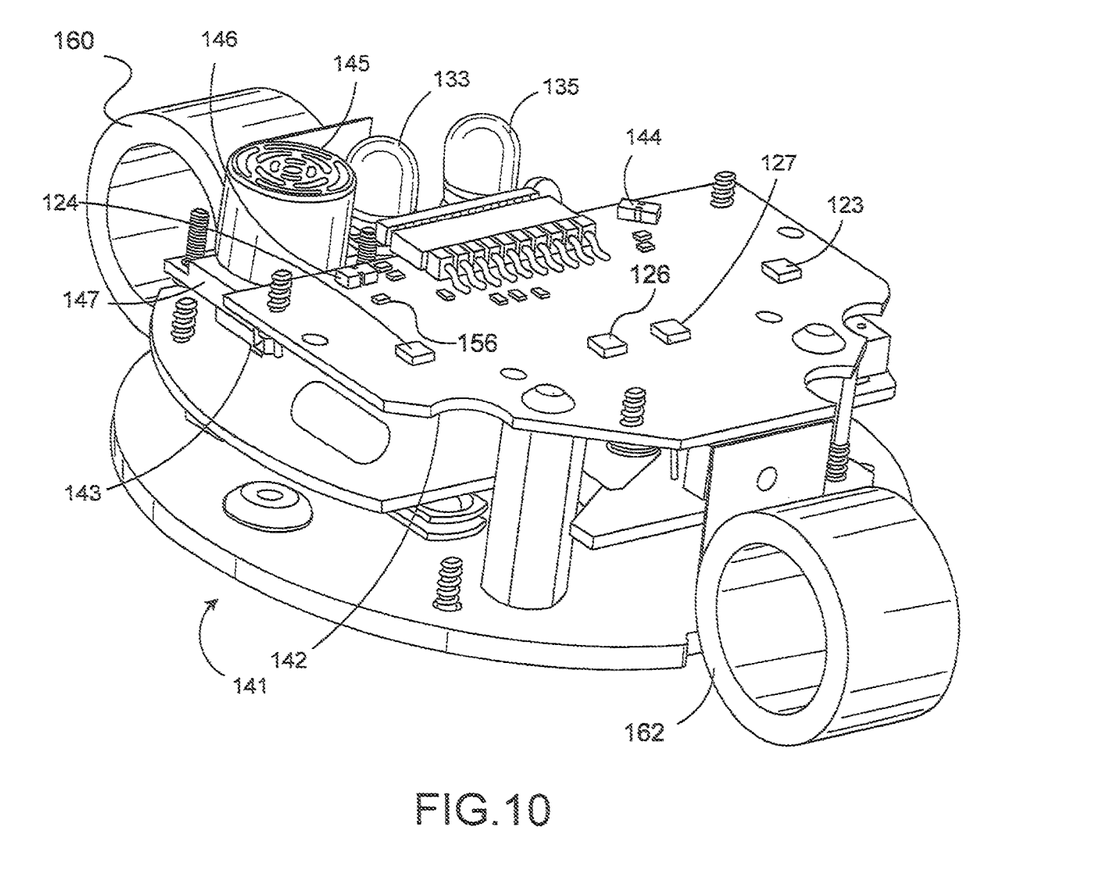
FIG. 10 is a perspective view of a mounting assembly of the second embodiment.

The top surface is provided with a plurality of openings which register with the components of the assembly as described below. Openings or apertures 118,120 are provided on the top surface 114 through which spot or narrow beam LEDs 123,124 project. Also, as shown in FIGS. 7A and 10, an enlarged opening 122 is provided in the top surface 114 through which the beam of "flood" or broad beam LEDs 126,127 are emitted. The narrow beam LEDs are high intensity LEDs used to scrub the aisles when the aisles are unoccupied.

The broad beams are used for continuous disinfecting of the interior of the space whether occupied or not but at a lower or safe irradiance limit.

A transparent cover 136 is disposed over the opening 122.

Figure 8:
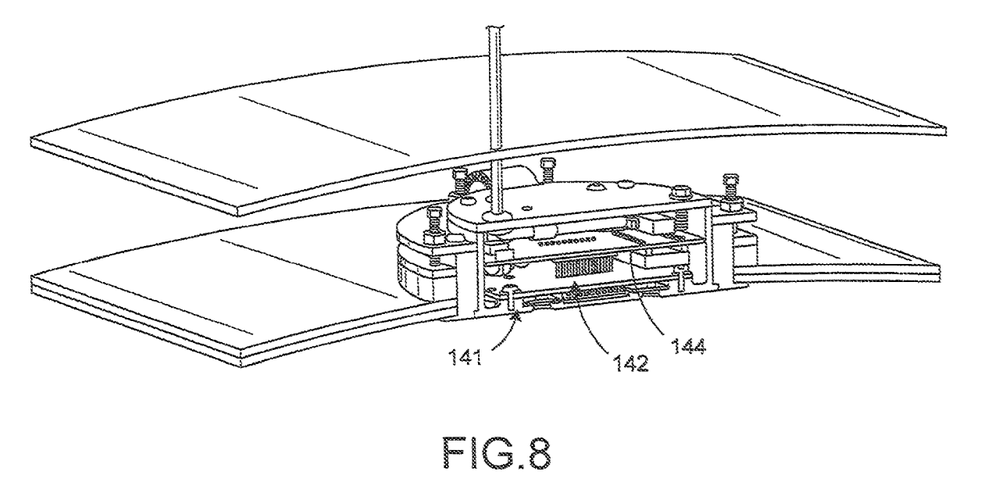
FIG. 8 is a cut away view of the mounting assembly disposed within the housing used in the second embodiment hereof.

As shown in FIGS. 8 and 10, and as referenced above, a mounting assembly 141 is disposed in the interior and to which the various components are secured. The assembly includes an LED board 142, a pcBoard or controller board 142 and a pad 147.

An ultrasound sensor 149 is disposed on the pad 147. The sensor 149 detects the presence or absence of an occupant for determining whether high intensity or low intensity irradiance is to be used.

The passive infrared sensors (PIR) 133,135 are used to sense the absence or presence of a person in the beam and are also secured to the controller board. The beams from the sensors 133,135 are emitted through openings 129,131. Similarly, range sensors 144 and 146, preferably LiDar sensors, are mounted to the pcBoard 142 and are used for sensing the absence or presence of a person within the aisle of the aircraft. The beams from these sensors are emitted through openings 144',146'.

The flood LEDs 126,127 are mounted to the pcBoard 142 and are aligned with the enlarged opening 122.

The ultrasound field of view sensor 145 is secured to the pad 147 and extends through a cover opening 149 provided on the surface 114.

In deploying the present device diametrically opposed retention springs 160,162 seated in respective seats 178,180 are secured to the side wall of the housing and are used to provide constant force against the aircraft headliner 170, as detailed below, once the device is installed.

Similar to the first embodiment, preferably, one LED indicator light 156 is provided which enables visual observation of the status of the device. The LED 156 is mounted to the LED board and projects its beam through an opening (not shown) provided on the surface or plate 114.

Optionally, a mode switch 182 may be installed which can dictate which disinfecting mode, i.e., the aisle scrub or the flood or both are to be rendered operational.

Figure 9:
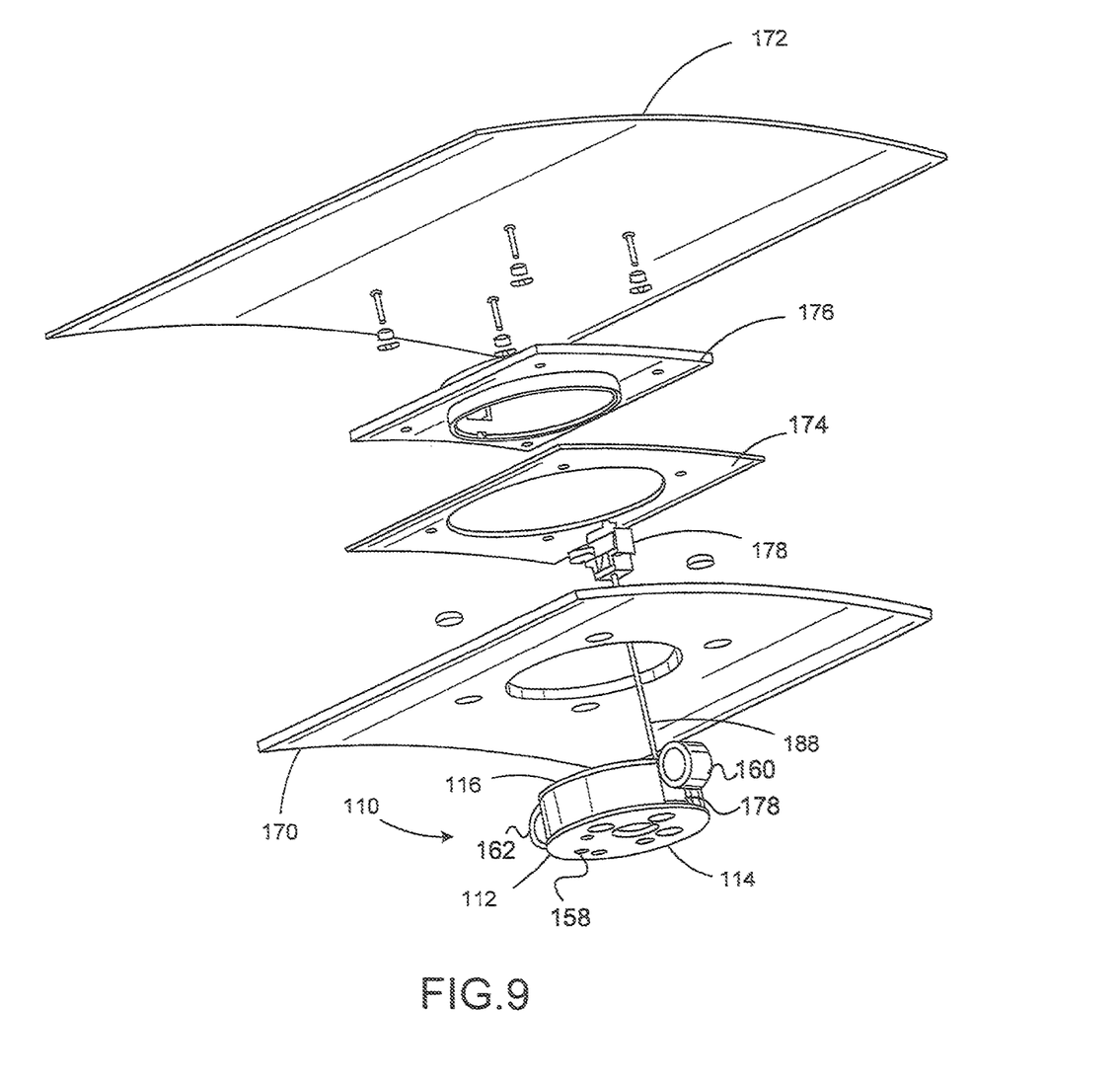
FIG. 9 is an exploded view showing the installation of the device thereof within an aircraft.

As shown, a pair of diametrically opposed seats 178,180 (FIG. 7B) are formed in the sidewall 115 of base 114. In deploying or installing the device, and as shown in FIGS. 8 and 9 suitable openings are provided in an airplane headliner 170 to enable the installation of the device therethrough.

As with the first embodiment, the device is disposed between the aircraft skin and a conventional airplane headliner.

Preferably, an installation shim 174 and bezel 176 are interposed the headliner 170 and the aircraft skin 172 to secure the device in position. The retention springs 160,162 maintain the device in position.

As with the first embodiment a power source or cable 188 is in electrical communication with the pcBoard and transmits the requisite power thereto.

The device, itself, is manufactured by any suitable means, such as by injection molding, additive manufacturing or the like and from any suitable materials which are FAA compliant, such as for example, thermoplastics, including ABS/PVC which are durable, chemical and fire resistant, as well as explosion proof and vibration or compression resistant. Preferably, the cover and base are formed from FAA approved T6 aircraft aluminum, although other metals may be used.

It should be noted that the present device can be modified to emit both UV-A and UV-C light.

As noted above, in deploying the present device, when occupied by passengers, the UV-C wavelength must be regulated to preclude injury to both the skin and the eyes and, therefore, lies in a defined range and for selected periods of time, as well as selected or pre-determined dosages.

The UV-C light will be at a preferred wavelength of between about 225 to about 325 nM and is typically emitted by one or more LEDs at a wavelength of between about 250 to 300 nM.

In use, as a default setting, the irradiance is normally set to administer the safe 'Actinic Dose' over a full 24 hours, since a human can be exposed to this irradiance continually, e.g., over a 24-hour period for overseas flights, per the IEC specification.

Figure 12:
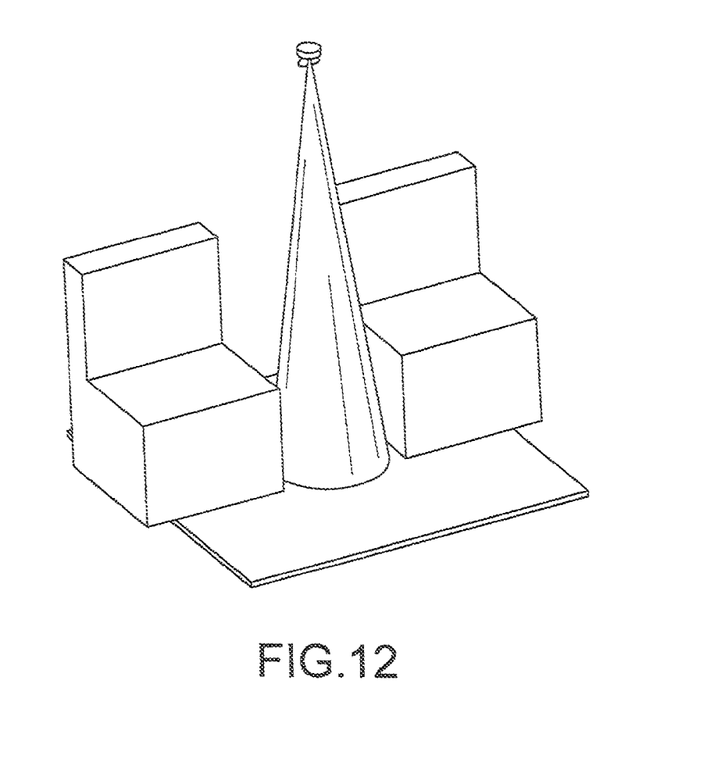
FIG. 12 is a geographical display showing the irradiance when an aircraft cabin is occupied.

FIGS. 11 and 12 illustrate the irradiance provided when the present device is deployed. The narrow beam LEDs emit three beams down the aisle of the aircraft while the "flood" or broad field beams irradiate the seats and other portions of the aircraft including side panels, when the seats are unoccupied.

Although not shown a controller for administering the 'Actinic Dose' in less than 24 hours, so that irradiance can be set higher with this lower exposure time and the efficacy of the higher irradiance may be included and which will destroy viruses more rapidly while reducing the potential for inter-passenger infectivity. This is accomplished by calculating the total time that passengers and crew may be within the aircraft that day and increasing the irradiance by a factor of 24 divided by the number of hours. Preferably, this is conducted by secure panel adjustments.

It is to be appreciated that if the aircraft is completely unoccupied, the UV-C LED may provide irradiance over the unoccupied time above the Actinic "dose" safe limit, because there are no humans/animals in harm's way. This enables a complete 'scrub' of the cabin in a very short time (e.g., in-between flights) so as to disinfect not only any aerosols but also surfaces (e.g., 'fomites' such as microscopic dried mucus/blood, likely harboring bacteria/endospores instead of the simpler viruses). Preferably, this is conducted by secure panel adjustments outside the aircraft.

In practicing the present invention, an excimer(s) may be used in lieu of the LED bulb(s).

It should, also, be noted that it is also possible to integrate a UV-A lamp hereinto to provide 'blended' disinfecting.

Also, it is to be understood that the present device can be used in other closed environments.

It is to be further appreciated that selection of all materials is highly constrained by FAA regulations to include only proven-nonflammable materials.

It is to be appreciated that there has been described herein a device which safely disinfects the interior of an occupied aircraft against viruses including the COVID-19 RNA-virus, but also many others, such as Influenza viruses.

Having, thus, described the invention, what is claimed is:

The invention claimed is:

1. A confined space UVC disinfecting device, comprising:
a housing having a top surface, a bottom cover plate and a substantially cylindrical sidewall therebetween, the top surface, the bottom surface, and sidewall cooperating to provide an interior chamber, a top surface having a pair of spaced-apart first openings, a second pair of spaced-apart openings and a third enlarged opening, a pair of UVC emitting bulbs projecting through the first pair of openings, a flood LED for emitting light through the enlarged opening, at least a pair of PIR sensors projecting through associated means in the top surface and a motion sensor secured to the top surface for detecting the absence or presence of a human and/or animal, and wherein the LEDs are UVC LEDs for disinfecting an interior of a closed space.

2. The device of claim 1 which further comprises a status light for indicating if the UVC LEDs are emitting light.

3. The device of claim 1 which further includes a mounting plate disposed within the interior of the device, and secured to the top surface, the PIR sensors the LEDs being mounted to the mounting plate and projecting through associated openings in the top surface being mounted to the plate and a pcBoard for controlling the operation of the LEDs.

4. The device of claim 1 which further includes a controller for controlling the amount of Actinic Dose emitting into the area to be disinfected, depending on the absence or presence of a human therewithin.

5. The device of claim 1 which further includes means for electrically connecting the device to the source of electricity.

6. In combination with an aircraft, the device of claim 1, and wherein the PIR sensors control the emission of the UVC light depending upon the absence or presence of a human within the field of irradiation of the flood LEDs.

7. The device of the combination of claim 6 which further includes a bezel surrounding a pair of diametrically opposed retention springs for holding the housing in position, a collar for securing the housing to a surface.

8. The device of claim 7 wherein the device is mounted to the ceiling or sidewall of the aircraft.

9. The housing of claim 8 which further comprises at least one PIR sensor secured to the mounting plate and projecting through an opening formed in the top surface, the PIR and Li Dar sensors being used to detect the presence or absence of a person or animal within the range of the LEDs.

* * * * *